United States Patent [19]

Kessel

[11] Patent Number: 5,654,498
[45] Date of Patent: Aug. 5, 1997

[54] DEVICE FOR THE SELECTIVE DETECTION OF A COMPONENT IN A GAS MIXTURE

[75] Inventor: Robert Kessel, Bad Oldesloe, Germany

[73] Assignee: Drägerwerk Aktiengesellschaft, Lübeck, Germany

[21] Appl. No.: 595,217

[22] Filed: Feb. 1, 1996

[30] Foreign Application Priority Data

Mar. 14, 1995 [DE] Germany ............... 195 09 146.9

[51] Int. Cl.$^6$ ............... G01N 27/16; G01N 1/22; H01J 27/00
[52] U.S. Cl. ............... 73/31.07; 73/23.2; 73/31.02; 324/464
[58] Field of Search ............... 73/31.07, 23.2, 73/31.02, 31.05, 31.06; 324/464

[56] References Cited

U.S. PATENT DOCUMENTS

| | | | |
|---|---|---|---|
| 3,438,241 | 4/1969 | McKinley, Jr. | 73/23 |
| 3,811,319 | 5/1974 | Arnold | 73/23 |
| 4,413,185 | 11/1983 | Leveson et al. | 250/423 P |
| 4,633,704 | 1/1987 | Tantram et al. | 73/23 |
| 4,670,405 | 6/1987 | Stetter et al. | 436/151 |
| 4,745,796 | 5/1988 | Abdelrahman et al. | 73/26 |
| 4,759,210 | 7/1988 | Wohltjen | 73/23 |
| 4,958,529 | 9/1990 | Vestal | 73/864.81 |
| 5,054,328 | 10/1991 | Long et al. | 73/864.81 |
| 5,319,955 | 6/1994 | Chastagner | 73/19.02 |
| 5,394,092 | 2/1995 | Wentworth et al. | 324/464 |

OTHER PUBLICATIONS

Drägerwerk Aktiengesellschaft Lübeck, 1994, Boden–Wasser– und Luftuntersuchungen sowie technische Gasanalyse, Dräger–Röhrchen Handbuch, No Translation.

*Primary Examiner*—Hezron E. Williams
*Assistant Examiner*—J. David Wiggins
*Attorney, Agent, or Firm*—McGlew and Tuttle

[57] ABSTRACT

A device for the selective detection of a component from a gas mixture comprises a selective prefilter for retaining the other components of the gas mixture, a measuring unit arranged downstream of the selective prefilter for the component to be detected, and a pump pumping the gas mixture. The use of a photoionization detector as a downstream measuring unit makes possible a continuous display operation.

19 Claims, 2 Drawing Sheets

DEVICE FOR THE SELECTIVE DETECTION OF A COMPONENT IN A GAS MIXTURE

FIELD OF THE INVENTION

The present invention pertains to a device for the selective detection of a component from a gas mixture with at least one selective prefilter for retaining the other components of the gas mixture, with a measuring unit arranged downstream of the selective prefilter for one component of the gas mixture, and with a pump pumping the gas mixture.

BACKGROUND OF THE INVENTION

A device of this type has become known from the DE journal *Dräger-Röhrchen-Handbook*[Dräger Tube Handbook], 1994, 9th edition, p. 89, as the "Dräger Tube Benzene 2/a." The selective detection of benzene in a benzene/toluene/xylene mixture is possible with such a device. The sample gas flow is fed through a prefilter into a display unit by means of a pump. Toluene and xylene react chemically with the filling in the prefilter and they are bound. The benzene component is detected in the display unit.

At least the display unit must be replaced after each measurement in the prior-art device.

SUMMARY AND OBJECTS OF THE INVENTION

The primary object of the present invention is to use a display unit which makes possible a continuous display operation.

This object is accomplished according to the invention with a device for the selective detection of a component from a gas mixture with at least one selective prefilter for retaining the other components of the gas mixture, with a measuring unit arranged downstream of the selective prefilter for one component of the gas mixture, and with a pump pumping the gas mixture. The measuring unit is a photoionization detector.

The pump is preferably arranged behind the photoionization detector in the direction of the gas flow, and the photoionization detector preferably has a discharge opening for a gas flow to pass therethrough towards the pump.

Preferably at least one selective prefilter is provided for retaining methane and/or water, arranged in front of the photoionization detector. The device is preferably used for the selective detection of benzene from a gas mixture with at last toluene and/or xylene as other components.

The advantage of the present invention, is essentially the fact that a photoionization detector (PID), which can be used according to the state of the art only for a summary detection of a mixture of different components, can now also be used for a selective, component-specific detection.

One advantageous application of the device according to the present invention is to detect benzene in a mixture containing at least toluene. This mixture may also contain xylene.

Two exemplary embodiments of the present invention are shown in the two figures and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
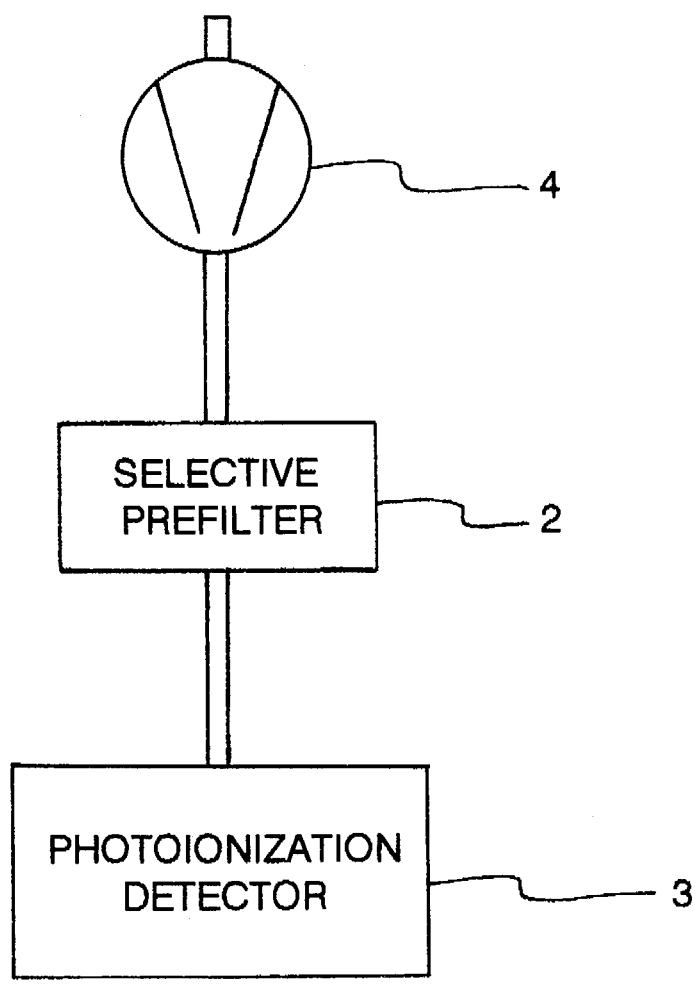
FIG. 1 is a schematic view of the detection device according to the invention.

FIG. 1 shows the device comprising a series connection of a selective prefilter 2 in the form of a reaction filter, a PID 3, and a pump 4, which pumps the sample gas flow. Benzene is to be selectively detected with the device in a benzene/toluene gas mixture.

The mode of operation of the device is as follows: Toluene and xylene are chemically bound in the known manner in the selective prefilter 2 designed as a reaction filter, and only benzene reaches the PID 3 as the component to be detected. The display on the PID 3 is proportional to the concentration in the gas mixture. Contrary to the state of the art, continuous measurement during the entire service life of the reaction filter is thus possible. The measurement must be interrupted only when the reaction filter has been consumed, which is indicated by a specific color reaction. This service life is 5,000 ppm×minute, so that measurement times of 30 minutes or more are possible, depending on the concentration of the gas or gases to be filtered out. In addition to the said prefilter, other selective filters, especially for water and methane, would also be used, because both gases greatly weaken the signal of the PID detector 3.

Figure 2:
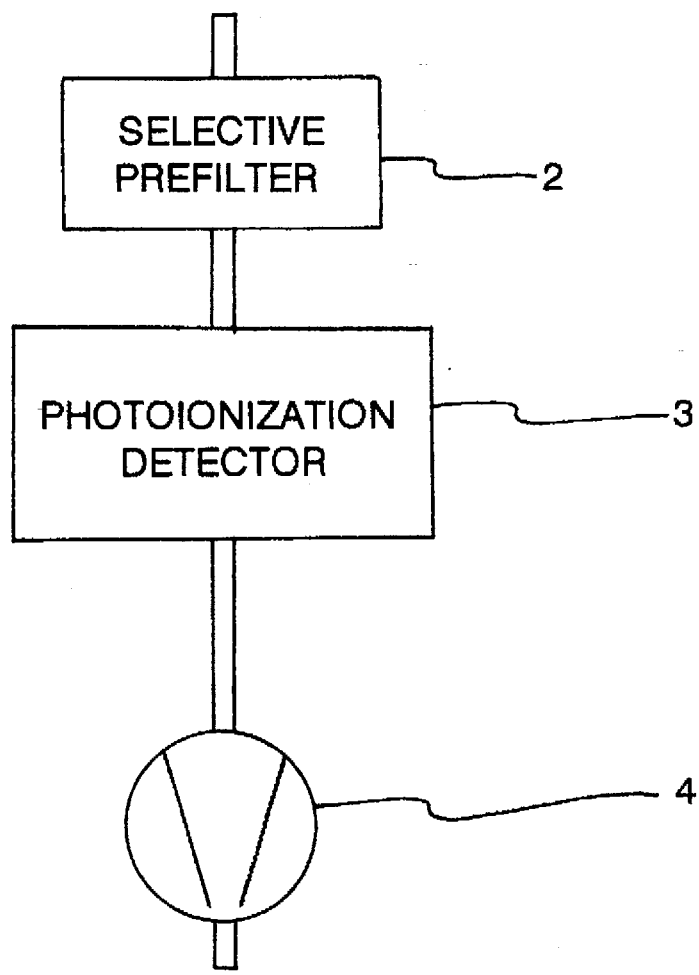
FIG. 2 is a schematic view of another embodiment of the invention.

FIG. 2 shows an alternative arrangement compared with FIG. 1. The pump 4 is located behind the PID 3 in this case. The other components are chemically bound in the selective prefilter 2 designed as a reaction filter, and only the component of interest reaches the PID 3 as the component to be detected. The display on the PID 3 is proportional to the concentration in the gas mixture. This arrangement offers the advantage that contamination of the gas by the pump 4 before the measurement of the gas does not take place. However, this variant requires that the PID 3 have a discharge opening for the gas flow in this case.

While specific embodiments of the invention have been shown and described in detail to illustrate the application of the principles of the invention, it will be understood that the invention may be embodied otherwise without departing from such principles.

What is claimed is:

1. A device for the selective detection of a component from a gas mixture containing other components in a gas flow having a flowpath from an upstream location to a downstream location, the device comprising:

at least one selective prefilter disposed in said flow path for retaining the other components of the gas mixture upon becoming chemically bound, and passing on said selected component in a downstream direction;

selective component specific measuring means comprising a measuring unit arranged downstream of the said selective prefilter for selectively detecting said one component of the gas mixture, said measuring unit including a photoionization detector; and a pump pumping the gas mixture in said downstream direction.

2. A device in accordance with claim 1, wherein said pump is arranged downstream of and behind said photoionization detector in the direction of the gas flow, and said photoionization detector has a discharge opening for passage of gas flow therethrough.

3. A device in accordance with claim 1, wherein said at least one selective prefilter is a prefilter for retaining methane and water and is arranged upstream of and in front of said photoionization detector.

4. A device in accordance with claim 1, wherein said at least one selective prefilter is a prefilter for retaining methane and is arranged upstream of and in front of said photoionization detector.

5. A device in accordance with claim 1, wherein said at least one selective prefilter is a prefilter for retaining water and is arranged upstream of and in front of said photoionization detector.

6. A device in accordance with claim 1 wherein said detector is for the selective detection of benzene from a gas mixture with at least toluene and/or xylene.

7. A process for the selective detection of a component from a gas mixture containing other components in a gas flow having a flowpath from an upstream location to a downstream location, the process comprising the steps of:
   providing a gas mixture with at least toluene and/or xylene;
   selectively detecting for a benzene component by
      providing at least one selective prefilter for retaining the toluene and/or xylene components of the gas mixture upon becoming chemically bound, and passing on said benzene component in a downstream direction,
      providing a measuring unit arranged downstream of the said selective prefilter, said toluene and/or xylene components of the gas mixture being retained by said prefilter at a location upstream of said measuring unit,
      measuring benzene as a component of the gas mixture, said measuring unit including a photoionization detector, wherein said step of measuring takes place with said photoionization detector and
   pumping the gas mixture in a downstream direction.

8. A process according to claim 7, wherein said step of pumping includes arranging a pump downstream of and behind said photoionization detector in the direction of the gas flow, and providing said photoionization detector with a discharge opening for passage of gas flow therethrough.

9. A device for the selective detection of a component from a gas mixture containing other components in a gas flow having a flowpath from an upstream location to a downstream location in the direction of a photoionization detector, the device comprising:
   at least one selective prefilter disposed in said flow path for retaining methane and water components of said gas mixture upon becoming chemically bound, and passing on said methane and water components in a downstream direction, said prefilter being arranged upstream of and in front of said photoionization detector;
   selective component specific measuring means arranged downstream of said selective prefilter for selectively detecting said one component of the gas mixture, said measuring means including a photoionization detector; and
   a pump pumping the gas mixture in said downstream direction.

10. A device in accordance with claim 9, wherein said pump is arranged downstream of and behind said photoionization detector in the direction of the gas flow, and said photoionization detector has a discharge opening for passage of gas flow therethrough.

11. A device in accordance with claim 9 wherein said detector is for the selective detection of benzene from a gas mixture with at least toluene and/or xylene.

12. A device for the selective detection of a component from a gas mixture containing other components in a gas flow having a flowpath from an upstream location to a downstream location, the device comprising:
   at least one selective reaction prefilter disposed in said flow path for retaining the other components of the gas mixture by chemically reacting with the other components of the gas mixture, and passing on said selected component in a downstream direction;
   selective component specific measuring means comprising a measuring unit arranged downstream of the said selective prefilter for selectively detecting said one component of the gas mixture, said measuring unit including a photoionization detector; and
   a pump pumping the gas mixture in said downstream direction.

13. A device in accordance with claim 12, wherein said pump is arranged downstream of and behind said photoionization detector in the direction of the gas flow, and said photoionization detector has a discharge opening for passage of gas flow therethrough.

14. A device in accordance with claim 12, wherein said at least one selective reaction prefilter is a prefilter for retaining methane and water and is arranged upstream of and in front of said photoionization detector.

15. A device in accordance with claim 12, wherein said at least one selective reaction prefilter is a prefilter for retaining methane and is arranged upstream of and in front of said photoionization detector.

16. A device in accordance with claim 12, wherein said at least one selective reaction prefilter is a prefilter for retaining water and is arranged upstream of and in front of said photoionization detector.

17. A device in accordance with claim 12 wherein said detector is for the selective detection of benzene from a gas mixture with at least toluene and/or xylene.

18. A device in accordance with claim 1, wherein said prefilter is a selective reaction prefilter disposed in said flow path, for retaining the other components of the gas mixture by chemically reacting with the other components of the gas mixture.

19. A device in accordance with claim 7, wherein said prefilter is a selective reaction prefilter disposed in said flow path for retaining the other components of the gas mixture by chemically reacting with the other components of the gas mixture.

* * * * *